(12) United States Patent
Smith

(10) Patent No.: US 6,413,250 B1
(45) Date of Patent: Jul. 2, 2002

(54) CATHETER SNAPPED VALVE

(75) Inventor: Eric Julian Henry MacLeod Smith, Cape Town (ZA)

(73) Assignee: Eric Oliver MacLeod Smith Family Trust, Constantai (ZA)

( * ) Notice: Subject to any disclaimer, the term of this patent is extended or adjusted under 35 U.S.C. 154(b) by 0 days.

(21) Appl. No.: 09/485,487

(22) PCT Filed: Aug. 10, 1998

(86) PCT No.: PCT/IB98/01221

§ 371 (c)(1),
(2), (4) Date: Feb. 11, 2000

(87) PCT Pub. No.: WO99/07430

PCT Pub. Date: Feb. 18, 1999

(30) Foreign Application Priority Data

Aug. 11, 1997 (ZA) ................................................ 97/7126

(51) Int. Cl.[7] ........................ A61M 25/16; A61M 25/18; A61M 39/00; A61M 39/10

(52) U.S. Cl. ............. 604/533; 604/167.01; 604/167.02; 604/250; 604/256

(58) Field of Search ................................ 604/264, 272, 604/167.01, 167.03, 256, 250, 246, 34, 30, 33, 167.02, 167.06, 249, 288.03, 533, 537; 251/4, 9

(56) References Cited

U.S. PATENT DOCUMENTS

| 3,565,078 A | * | 2/1971 | Livingston et al. .......... 604/537 |
| 4,874,377 A | * | 10/1989 | Newgard et al. ....... 604/167.02 |
| 5,385,560 A | * | 1/1995 | Wulf ..................... 604/167.02 |

* cited by examiner

Primary Examiner—Charles R. Eloshway
Assistant Examiner—Tuan Nguyen
(74) Attorney, Agent, or Firm—Young & Thompson

(57) ABSTRACT

A cannula valve arrangement made from a suitably resilient polymeric material including a body (10) having a substantially cylindrical cavity (16) for receiving a medical apparatus hub (32, 34) and a sleeve (14) having a bore (18) for receiving a cannula (28), which is open into the body cavity. A zone (20) of the body wall which defines the cavity (16) is convexly bulged from the body (10) and is adapted to snap from its convex shape into a concave shape in the body cavity (16) when pressed over-center into the body to close the bore (18) of the sleeve (14) to the cavity until again moved outwardly from the cavity (16).

8 Claims, 2 Drawing Sheets

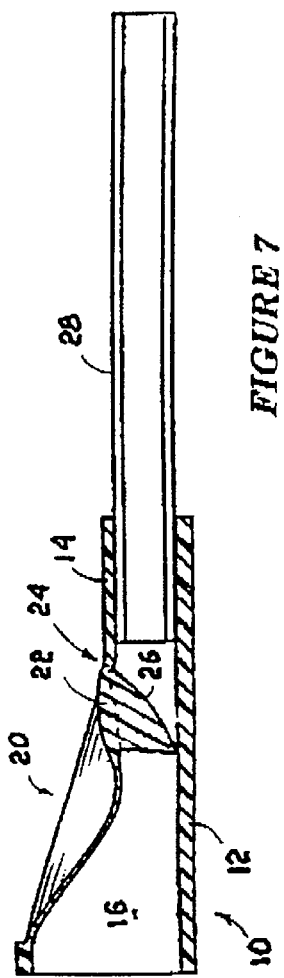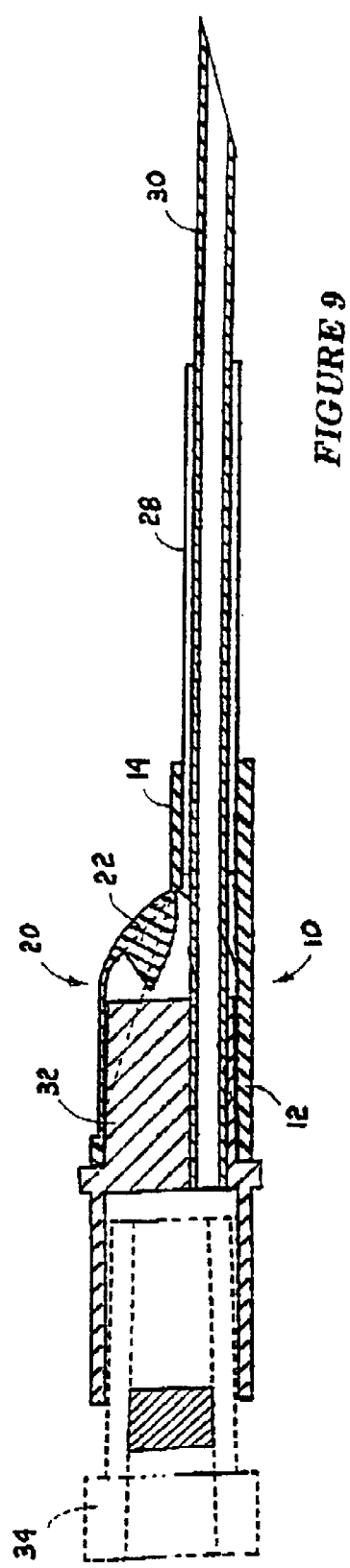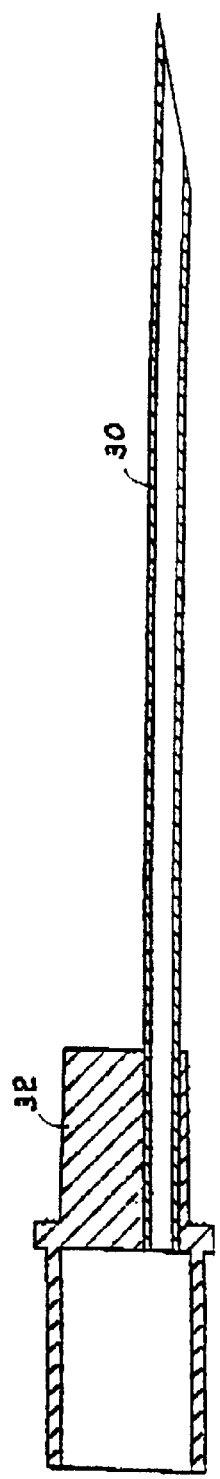

CATHETER SNAPPED VALVE

FIELD OF THE INVENTION

This invention relates to a shut-off valve arrangement for occluding the flow of a fluid through the bore of a cannula.

In this specification the term cannula is intended to include a catheter or any other conduit for introducing liquid into or draining fluid from the body of a patient.

BACKGROUND TO THE INVENTION

Various valve arrangements for occluding the flow of a body fluid through a fluid flow or infusion instrument are well known. Most of the known valve arrangements generally fall into two classes: those which include few components and are so inexpensive and those which include several separately manufactured components which require to be assembled and which are consequently more expensive. Typical examples of the valve arrangements of the first type are those disclosed in U.S. Pat. Nos. 4,198,973 and 5,429,616 which pinch the fluid bore in a catheter or cannula closed by some finger operated mechanism and which again opens the passage when the finger pressure on the mechanism is released. Although these valve arrangements are relatively cheap compared to the valve arrangements of the second type they require hands-on operation while closing the fluid passage of the conduit to which they are connected so restricting free hand use of the person who is inserting or removing the catheter or cannula into or from the body of a patient.

OBJECT OF THE INVENTION

It is the object of this invention to provide a simple single piece cannula valve arrangement which is simply closed for hands-off insertion into or removal from the body of a patient.

SUMMARY OF THE INVENTION

A cannula valve arrangement which is made from a suitably resilient polymedic material including a body having a substantially cylindrical cavity for receiving a medical apparatus hub and a sleeve having a bore, for receiving a cannula, which is open into the body cavity according to the invention is characterised in that a zone of the body wall which defines the cavity is convexly bulged from the body and has a wall thickness which is less than that of the remainder of the body to enable the bulged portion of the body to snap from its convex shape into a concave shape in the body cavity when pressed over-centre into the body to close the bore of the sleeve to the cavity until again pressed outwardly from the cavity.

The diameter of the catheter sleeve bore may be significantly less than the diameter of the portion of the body which defines the cylindrical cavity with the axis of the sleeve bore being parallel to and eccentrically displaced from the axis of the cylindrical cavity with a transition portion of the body between the cylindrical cavity portion and the sleeve defining the bulged zone of the body.

The mouth of the cannula sleeve bore in the cylindrical cavity conveniently defines a valve seat and the inner surface of the bulge zone of the body carries an inwardly projecting valve member which when the bulged portion of the body is pressed into the cylindrical cavity closes the sleeve bore. The junction between the bulged portion of the body and the sleeve is preferably made in the form of a plastic hinge which is linear and normal to the direction of the cylindrical cavity and the sleeve bore axes.

The valve arrangement preferably includes a cannula which is fixed to the body sleeve with its bore in alignment with the sleeve bore.

The valve arrangement may include a needle which is eccentrically located in a hub with the needle projecting from the cannula and the hub located in the cylindrical cavity of the body with its leading end clear of the valve member in the cavity.

The invention additionally extends to a needle for use with the valve arrangement of the invention.

BRIEF DESCRIPTION OF THE DRAWINGS

An embodiment of the invention is now described by way of example only with reference to the drawings in which:

FIG. 7 is a sectioned side elevation of the valve arrangement body shown in the closed position of the valve and including a cannula, FIG. 8 is a sectioned side elevation of a needle and hub for use with the valve arrangement of the invention, and FIG. 9 is a sectioned side elevation of the valve arrangement of the invention ready for use.

DETAILED DESCRIPTION OF THE PREFERRED EMBODIMENT

Figure 1:
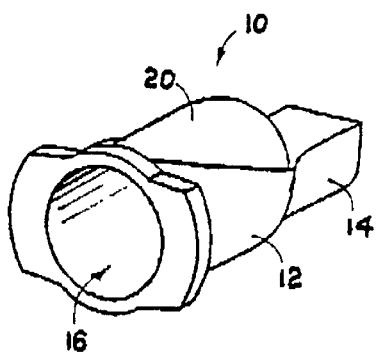
FIG. 1 is a perspective view of the valve arrangement body of the invention as seen from the front, above and one side.
Figure 2:
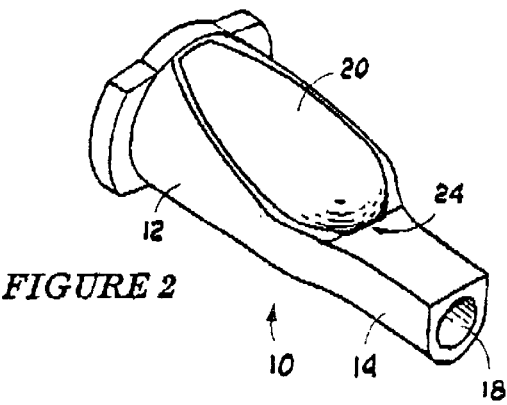
FIG. 2 is a similar view to that of FIG. 1 illustrating the valve arrangement body from the rear.
Figure 6:
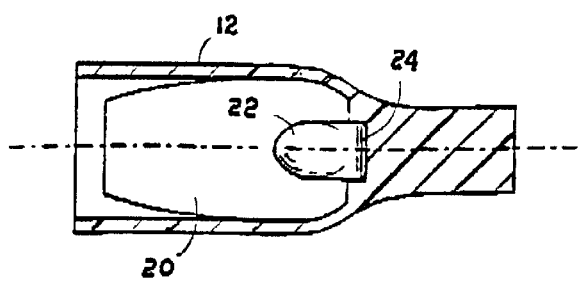
FIG. 6 is a under plan view of the FIG. 3 body shown sectioned on the line 6—6 in FIG. 3.

The valve arrangement of the invention is shown in the drawings to include a body 10 which is composed of a cylindrical body portion 12 and a cannula sleeve 14. The cylindrical portion 12 of the body is open at the forward end of the body and closed at its rear end to define a cylindrical cavity 16 with the bore 18 of the sleeve portion 14 of the sleeve being in communication with the cavity 16 as is shown in FIG. 3.

The valve arrangement body 10 is moulded economically in one piece, using a single core mould, from a resilient medical grade plastic material such as polypropylene, nylon or the like. It may, however, be made from a suitable rubber or like material which has the required stiffness and resilience for its operation as will be explained below.

Figure 3:
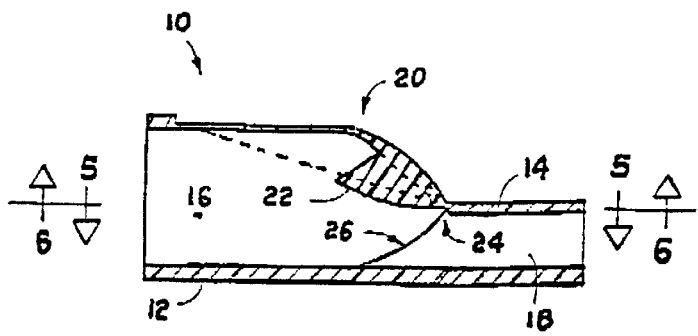
FIG. 3 is a sectioned side elevation of the valve arrangement body.
Figure 4:
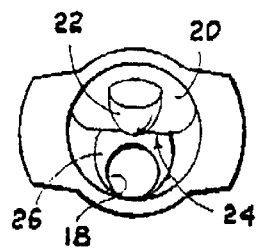
FIG. 4 is an end elevation of the FIG. 3 body.
Figure 5:
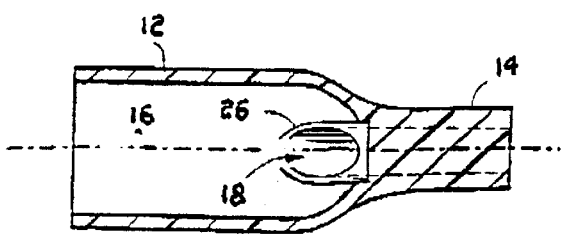
FIG. 5 is a plan view of the FIG. 1 body shown sectioned on the line 5—5 in FIG. 3.

As is best appreciated from FIG. 3 the cylindrical portion 12 of the body has a significantly greater diameter, which is engageable with conventional LUER slip medical hub spigots, than the vertical cross-sectional dimension of the sleeve 14. The upper rear surface portion of the body portion 12 is convexly curved downwardly onto the flattened upper surface of the sleeve 14. The portion of the wall of the cylindrical portion 12 of the body, above the upwardly inclined dotted line in FIG. 3, is thinned down to a smaller dimension than that of the remainder of the wall of the body portion 12 to provide what amounts to a resiliently flexible bulge zone 20 which includes, to the rear of its inner surface, an inwardly projecting valve member 22. The straight line junction position between the bulge zone 20 and the flat upper surface of the sleeve 14 is formed to provide a linear plastic hinge 24 which is normal to the axes of the cylindrical cavity 16 and the sleeve 14. The wall thickness of the bulge zone around the valve member 22 is slightly thickened relatively to the wall thickness of the upper forward part of the bulge zone.

The opening into the bore 18 of the sleeve 14 in the body cavity 16 is surrounded by a downwardly sloping slightly concave land 26 which, with the opening to the bore, defines a seat for the valve member 22.

A flexible cannula 28, shown in FIG. 7, is fixed in the sleeve 14 by means of a suitable adhesive with its bore in axial register with the sleeve bore.

A needle for use with the valve arrangement of the invention is illustrated in FIG. 8 and is shown in the drawing to include a conventional metal needle 30 which is eccentrically located in a conventional needle hub 32 to cater for the offset eccentricity of the axes of the cylindrical cavity 16 and the bore 18 of the sleeve 14 of the valve arrangement of the invention. As is seen in FIG. 9, the length of the body cavity 16 is such that the leading end of the needle hub 32 is clear of the valve member 22 when the hub is inserted fully into the cavity.

In use, for example in an intravenous drip procedure, a conventional air pervious blanking hub 34 is inserted into the needle hub 32 cavity as shown in FIG. 9. The needle 30 and cannula 28 are then located in the patient's vein. The transparent hub 34, as is conventional, serves as an indicator that the needle 30 is correctly located when it becomes blood filled. The person carrying out the procedure then presses down with a finger on the rear portion of the bulge zone 20 and withdraws the needle 30, together with the plug 34, from the patient. As the sharpened tip of the needle passes the valve member 22, which is pressed down on the needle 30 as it is withdrawn from the body 10, the bulge zone is pressed downwardly into the cavity 16 of the body 10 The bulge zone 20 obviously has a greater area than its more rigid surround, the dotted line in FIG. 3, and this larger area together with the fairly stiff resilience of the plastic material from which it is made causes the material of the bulge zone to snap into the body with an over-centre action as it is pressed inwardly beyond the dotted line position in FIG. 3. When the bulge zone 20 has snapped into the cavity 16 of the body the valve member 22 is closed firmly onto its seat 26 to obturate the sleeve bore 18 and that of the cannula 28 connected to it, as shown in FIG. 7, to prevent blood flow from the patient. The bulge zone 20 is held in its FIG. 7 closed position by the bowed spring effect of the material from which the body 10 is made.

An important feature of the invention is that the linear hinge 24 holds the valve member 22 against skewing while being moved from its open to its closed position of operation, even under a misdirected closing pressure, to ensure accurate and positive engagement of the valve member 22 with its seat.

An outlet hub from a conventional giving set is now pressed into the cavity 16 of the body 10 of the valve arrangement. On entering the cavity 16 the nose of the giving set hub will press against the forward end of the now concave bulge zone 20 with further pressure on the hub causing the bulge zone to be rolled upwardly until, under the resilience of its material, it is caused to snap out of the cavity 16 back to its FIG. 3 position and in so doing to open the fluid passage through the body 10 and the giving set conduit to the patient.

From the above description of the valve arrangement of the invention it will be appreciated that the one-piece body 10 is simple and inexpensive to manufacture and because of the positive and locked closing action of its valve member it enables the hands of the person carrying out the insertion procedure to be totally freed to perform tasks, other than pressing veins closed and so on, while connecting a giving set to the valve assembly of the invention.

The invention is not limited to the precise details as herein described. For example, the cylindrical portion 12 of the body 10 could be made longer than shown in the drawings and be made to include an infusion port. Additionally, to open the closed valve without having to press an object into the body cavity 16 the bulge zone 20 could be made to include a small trigger formation which in the FIG. 3 position of the bulge zone will project rearwardly from behind the valve member to be approximately parallel to the sleeve 14 and which in the FIG. 7 position of the bulge zone will point upwardly from where it may be pressed downwardly towards the sleeve 14 to snap the bulge zone out of the body cavity 16. Yet further, if the valve arrangement of the invention is to be used as a urinary catheter it would be moulded from a suitable rubber or rubber-like material with the sleeve 14 being considerably extended and suitably shaped in cross-section beyond the hinge 24 to provide the catheter.

What is claimed is:

1. A cannula valve arrangement which is made from a resilient polymeric material including a body (10) having a substantially cylindrical cavity (16) for receiving a medical apparatus hub (32,34) and a sleeve (14) having a bore (18) adapted to receive a cannula (28), which is open into the body cavity characterised in that the axis of the bore (18) is parallel to the axis of the cylindrical cavity (16), and that a zone (20) of a body wall which defines the cavity (16) may be snapped from a convexly bulged shape in which the end of the bore (18) is open to the cavity (16) into a concave shape in which the zone lies within the body cavity (16) and in which the zone closes the bore (18) of the sleeve (14).

2. The cannula valve arrangement as claimed in claim 1, wherein that the bulged zone (20) of the body (10) has a wall thickness which is less than the body wall thickness surrounding the bulged zone (20).

3. The cannula valve arrangement as claimed in claim 1, wherein the diameter of the sleeve bore (18) is significantly less that the diameter of the portion of the body (10) which defines the cylindrical cavity (16) with the axis of the sleeve bore (18) being eccentrically displaced from the axis of the cylindrical cavity (16) with a transition portion of the body between the cylindrical cavity portion (16) and the sleeve (14) defining the bulged zone (20) of the body (10).

4. The cannula valve arrangement as claimed in claim 1, wherein the mouth opening of the cannula sleeve (14) bore (18) in the cylindrical cavity (16) defines a valve seat and the inner surface of the bulge zone (20) of the body (10) carries an inwardly projecting valve member (22) which when the bulged portion (20) of the body is pressed into the cylindrical cavity (16) closes the sleeve bore (18).

5. The cannula valve arrangement as claimed in claim 4, wherein a junction between the bulged portion (20) of the body (10) and the sleeve (14) is in the form of a plastics hinge (24) which is linear and normal to the direction of the cylindrical cavity (16) and the sleeve bore (18) axes.

6. The cannula valve arrangement as claimed in claim 5, wherein the valve member (22) extends from the hinge (24) onto the inner surface of the bulge zone (20) of the body (10).

7. The cannula unit comprising a cannula valve arrangement as claimed in claim 1, and including a cannula (28)

which is fixed to the body sleeve (14) with its bore in alignment with the sleeve bore (18).

8. The cannula unit as claimed in claim 7 and including a needle (30) which is eccentrically located in a hub (32) with the needle (30) projecting from the cannula (28) and the hub (32) located in the cylindrical cavity (16) of the body (10) with its front end clear of the valve member (22) in the cavity (16).

* * * * *